(12) United States Patent
Mullen et al.

(10) Patent No.: US 7,015,317 B2
(45) Date of Patent: Mar. 21, 2006

(54) POLYNUCLEOTIDES FOR THE DETECTION AND QUANTIFICATION OF HEPATITIS B VIRUS NUCLEIC ACIDS

(75) Inventors: Carolyn Mullen, Libertyville, IL (US); James Rhoads, Mundelein, IL (US)

(73) Assignee: Abbott Laboratories, Downers Grove, IL (US)

( * ) Notice: Subject to any disclaimer, the term of this patent is extended or adjusted under 35 U.S.C. 154(b) by 298 days.

(21) Appl. No.: 10/138,184

(22) Filed: May 2, 2002

(65) Prior Publication Data

US 2005/0164353 A1   Jul. 28, 2005

(51) Int. Cl.
   *C07H 21/00* (2006.01)
(52) U.S. Cl. .................. 536/24.3; 530/300; 900/10; 900/220; 900/223; 435/5; 435/6; 435/4; 435/29; 435/34; 435/39; 536/24.33
(58) Field of Classification Search ............... 530/300; 930/10, 220, 223; 435/5–6, 4, 29, 34, 39; 536/24.3, 24.33

See application file for complete search history.

(56) References Cited

U.S. PATENT DOCUMENTS

| | | | |
|---|---|---|---|
| 5,034,506 A | 7/1991 | Summerton et al. | |
| 5,142,047 A | 8/1992 | Summerton et al. | |
| 5,185,444 A | 2/1993 | Summerton et al. | |
| 5,196,194 A | * 3/1993 | Rutter et al. ............ | 424/189.1 |
| 5,627,030 A | 5/1997 | Pandian | |
| 5,736,316 A | 4/1998 | Irvine et al. | |
| 5,736,334 A | * 4/1998 | Spies ....................... | 435/6 |
| 5,827,661 A | 10/1998 | Blais | |
| 5,925,517 A | 7/1999 | Tyagi et al. | |
| 6,103,476 A | 8/2000 | Tyagi et al. | |
| 6,150,097 A | 11/2000 | Tyagi et al. | |

FOREIGN PATENT DOCUMENTS

| | | |
|---|---|---|
| EP | 0 583 798 | 4/1994 |
| EP | 0 860 505 | 8/1998 |
| WO | 92/20702 | 11/1992 |
| WO | 93/09233 | 5/1993 |

OTHER PUBLICATIONS

Sequence alignment of SEQ ID No. 1 with residues 15-40 of SEQ ID No.: 22 of Spies.*

Sequence alignment of SEQ ID No. 3 with Residues 35-9 of SEQ ID No.: 23 of Spies.*

Sequence alignment of SEQ ID No. 1 with Residues 246-271 of SEQ ID No.: 11 and residues 1652-1677 of SEQ ID No.: 15 of Rutter et al.*

Sequence alignment of SEQ ID No. 3 with Residues 438-412 of SEQ ID No.: 11 and residues 1844-1818 of SEQ ID No.: 15 of Rutter et al.*

Norder, H., et al., "Genetic relatedness of hepatitis B viral strains of diverse geographical origin and natural variations in the primary structure of the surface antigen", J. Gen. Virol, USA, 74, pp. 1341-1348 (1993).

Stuyver, L. et al. "A new genotype of hepatitis B virus: complete genome and phylogenetic relatedness", J. Gen. Virol, USA, 81, pp. 67-74 (2000).

Magnius L., et al. "Subtypes, genotypes and molecular epidemiology of the hepatitis B virus as reflected by sequence variability of the S-gene", Intervirology, USA, 38, pp. 24-34 (1995).

Martin, P., et al. "Ein neuer Zugang zu 2'-O-Alkylribonucleosiden und Eigenschaften deren Oligonculeotide", Helvetica Chemica Acta, Germany, 78, pp. 486-504 (1995).

Neilson, P., et al. "Sequence-selective recognition of DNA by strand displacement with a thymine-substituted polyamide", Science, USA, pp. 1497-1500 (1991).

Tgayi et al. "Multicolor molecular beacons for allele discrimination", Nature Biotechnology, USA, pp. 49-53 (1998).

Marras et al. "Multiplex detection of single-nucleotide variations using molecular beacons", Genetic Analysis: Biomolecular Engineering, USA, pp. 151-156 (1999).

* cited by examiner

*Primary Examiner*—Jeffrey S. Parkin
*Assistant Examiner*—Emily M. Le

(57) ABSTRACT

The present invention provides polynucleotides that can specifically hybridise to Hepatitis B virus (HBV) nucleic acids from all genotypes. These polynucleotides can be used in genotype-independent detection and quantitation of HBV nucleic acids. For example, the polynucleotides can be used as primers and/or probes in amplification-based assays for either end-point detection or real-time monitoring of HBV nucleic acids in a test sample. The polynucleotides can additionally be provided as part of a kit for the detection and quantitation of HBV nucleic acids.

7 Claims, No Drawings

POLYNUCLEOTIDES FOR THE DETECTION AND QUANTIFICATION OF HEPATITIS B VIRUS NUCLEIC ACIDS

FIELD OF THE INVENTION

The present invention pertains to the field of hepatitis B virus (HBV), in particular, to polynucleotides for use in detecting and quantitating HBV nucleic acids in a test sample.

BACKGROUND

Hepatitis B is the most common chronic infectious disease in the world. The hepatitis B virus (HBV) demonstrates considerable genetic diversity with seven genomic groups (designated genotype A through G) having been identified to date (Norder, H., et al., (1993) *J. Gen. Virol.,* 74:1341–1348; Stuyver, L. et.al., (2000) Journal of General Virology, 81:67–74). Each of these genotypes shows a characteristic geographical origin, and comprises several variant HBV genomes. Worldwide molecular diversity of HBV is based on the variability of the S-gene. The maximum genetic divergence of HBV genomes has been determined at 8% over the complete genome (Magnius, L. O. and Norder, H., (1995) *Intervirology,* 38:24–34).

Characterisation of HBV by genotype is fairly recent. Historically HBV was characterised on the basis of immunological reaction of the hepatitis B surface antigen (HBsAg) with sets of monoclonal antibodies. Isolates were described as "a," indicating the common determinant for all different subtypes, followed by the subtype specific combinations: dw, dr, yw, or yr. The latter are mutually exclusive pairs of determinants, covering the HBsAg amino acids 122 (d=lys, y=arg) and 160 (w=lys, r=arg).

Currently available methods to diagnose HBV infection are immunoassay-based techniques that rely on serological markers such as HbsAg, HbeAg, anti-HBc IgM, or anti-HBe, anti-HBs, or anti-HBc IgGs. Immunoassay techniques are by nature non-quantitative and, in addition, require detection of more than one serological marker in order to determine whether an individual is currently infected or has been infected in the past.

An assay capable of directly detecting HBV nucleic acids in the serum or plasma of an infected subject, rather than the presence of serological markers, would provide a distinct advantage over immunoassay techniques. For example, detection of serum levels of HBV nucleic acids would provide a means for direct quantitation of the amount of HBV present in a sample. With the advent of anti-viral therapy for the treatment of HBV infection, such direct quantitation of HBV in the serum or plasma has become essential in order to monitor the progress of this therapy.

Methods of detecting HBV nucleic acids have been previously proposed. For example, International Patent Application No. PCT/US93/09233 and European Patent Application Nos. 0 593 789 A1 and 0 860 505 A1 describe polymerase chain reaction (PCR) based assays for genotyping and detecting HBV, and U.S. Pat. No. 5,736,316 describes a sandwich hybridization assay for the detection of HBV nucleic acids. However, there is currently no single method available for detection of all known genotypes of HBV; most available techniques are purposely based on differences between genotypes thus allowing the genotypes to be distinguished. A need, therefore, exists for a method that allows detection of HBV nucleic acids regardless of genotype. Such a method would have worldwide applicability as a diagnostic tool. In addition, since currently available immunoassay techniques are not capable of measuring serum levels of viral nucleic acids, a need exists for a method that allows quantitative determination of HBV viral nucleic acids in an infected subject.

This background information is provided for the purpose of making known information believed by the applicant to be of possible relevance to the present invention. No admission is necessarily intended, nor should be construed, that any of the preceding information constitutes prior art against the present invention. Publications referred to throughout the specification are hereby incorporated by reference in their entireties in this application.

SUMMARY OF THE INVENTION

An object of the present invention is to provide polynucleotides that can hybridise to HBV nucleic acids from all genotypes. The polynucleotides can be used for the detection and quantitation of Hepatitis B virus nucleic acids. In accordance with an aspect of the present invention, there is provided an isolated polynucleotide, or analogue thereof, said polynucleotide having a nucleic acid sequence as set forth in any one of SEQ ID NOs: 1–30, or the complement, or homologues of these nucleic acid sequences, or combinations thereof.

In accordance with another aspect of the invention, there is provided a combination of polynucleotides, or analogues thereof, said combination comprising the nucleic acid sequences as set forth in: SEQ ID NOs: 1 and 3; SEQ ID NOs: 1 and 4; SEQ ID NOs: 5 and 7; SEQ ID NOs: 8 and 10; SEQ ID NOs: 11 and 13; or SEQ ID NOs: 14 and 16, or the complement or homologues of these nucleic acid sequences.

In accordance with another aspect of the invention, there is provided a combination of polynucleotides, or analogues thereof, said combination comprising the nucleic acid sequences as set forth in: SEQ ID NOs: 1, 2, and 3; SEQ ID NOs: 1, 2, and 4; SEQ ID NOs: 5, 6 and 7; SEQ ID NOs: 8, 9 and 10; SEQ ID NOs: 11, 12 and 13; SEQ ID NOs: 14, 15 and 16; SEQ ID NOs: 1, 3 and 17; SEQ ID NOs: 1, 3 and 18; SEQ ID NOs: 1, 3 and 19; SEQ ID NOs: 1, 3, and 20; SEQ ID NOs: 1, 4 and 17; SEQ ID NOs: 1, 4 and 18; SEQ ID NOs: 1, 4 and 19; SEQ ID NOs: 1, 4, and 20; SEQ ID NOs: 1, 3 and 21; SEQ ID NOs: 1, 3 and 26; SEQ ID NOs: 1, 3 and 27; SEQ ID NOs: 1, 3, and 28; SEQ ID NOs: 1, 3 and 29; SEQ ID NOs: 1, 3 and 30; SEQ ID NOs: 1, 4, and 21; SEQ ID NOs: 1, 4 and 26; SEQ ID NOs: 1, 4 and 27; SEQ ID NOs: 1, 4 and 28; SEQ ID NOs: 1, 4 and 29; SEQ ID NOs: 1, 4 and 30; SEQ ID NOs: 5, 7 and 22; SEQ ID NOs: 8, 10 and 23; SEQ ID NOs: 11, 13 and 24; SEQ ID NOs: 14, 16 and 25, or the complement or homologues of these nucleic acid sequences.

In accordance with another aspect of the present invention, there is provided a method of detecting Hepatitis B virus (HBV) nucleic acids in a test sample suspected of containing, or known to contain, one or more target HBV nucleic acid sequences comprising the steps of:
  a) contacting said test sample with at least one polynucleotide according to claim 1 under hybridising conditions; and
  b) detecting hybridization between said polynucleotide and the target HBV nucleic acid sequence, wherein the presence of hybridisation is indicative of the presence of HBV nucleic acids in said test sample.

In accordance with another aspect of the present invention, there is provided a method of amplifying Hepatitis B virus (HBV) nucleic acids in a test sample suspected of containing, or known to contain, one or more target HBV nucleic acid sequences comprising the steps of:
 a) forming a reaction mixture comprising nucleic acid amplification reagents, the test sample and at least one of the combinations of polynucleotides according to claim 1 or 2; and
 b) subjecting said mixture to amplification conditions to generate at least one copy of said target HBV nucleic acid sequence.

In accordance with another aspect of the present invention, there is provided a method of detecting Hepatitis B virus (HBV) nucleic acids in a test sample suspected of containing, or known to contain, one or more target HBV nucleic acid sequences comprising the steps of:
 a) forming a reaction mixture comprising nucleic acid amplification reagents, the test sample and at least one of the combinations of polynucleotides according to claim 1 or 2;
 b) subjecting said mixture to amplification conditions to generate at least one copy of said target HBV nucleic acid sequence;
 c) contacting the at least one copy of said target nucleic acid sequence with at least one probe consisting of a polynucleotide according to claim 1 under hybridizing conditions to form a probe:target hybrid, said probe being selected such that it is: i) different from the polynucleotides used in step a, and ii) complementary to a region of said target nucleic acid; and
 d) detecting the probe:target hybrid, wherein the presence of hybridisation is indicative of the presence of HBV nucleic acids in said test sample.

In accordance with another aspect of the present invention, there is provided a method of amplifying and detecting Hepatitis B virus (HBV) nucleic acids in a test sample suspected of containing, or known to contain, one or more target HBV nucleic acid sequences comprising the steps of:
 a) forming a reaction mixture comprising nucleic acid amplification reagents, the test sample and at least one of the combinations of polynucleotides according to claim 1 or 3, said combination consisting of polynucleotide primers and at least one polynucleotide probe;
 b) subjecting said mixture to amplification conditions to generate at least one copy of said target nucleic acid sequence;
 c) hybridising the polynucleotide probe to the target nucleic acid sequence to form a probe:target hybrid; and
 d) detecting the probe:target hybrid, wherein the presence of probe:target hybrid is indicative of the presence of Hepatitis B viral nucleic acids in said test sample.

In accordance with still another aspect of the present invention, there is provided a method of quantitating Hepatitis B virus (HBV) nucleic acids in a test sample known to contain at least one target HBV nucleic acid sequence comprising the steps of:
 a) forming a reaction mixture comprising nucleic acid amplification reagents, the test sample and at least one of the combinations of polynucleotides according to claim 1 or 3, said combination consisting of polynucleotide primers and at least one polynucleotide probe;
 b) subjecting said mixture to amplification conditions to generate at least one copy of said target nucleic acid sequence;
 c) hybridising the polynucleotide probe to the target nucleic acid sequence to form a probe:target hybrid;
 d) detecting the probe:target hybrid; and
 e) comparing the amount of probe:target hybrid to a standard, wherein comparing the amount of probe:target hybrid to a standard provides an indication of the amount of HBV nucleic acids present in the test sample.

In accordance with yet another aspect of the present invention, there is provided a method of monitoring Hepatitis B virus (HBV) viral load in the serum or plasma of a subject comprising the steps of:
 a) preparing a test sample of plasma or serum from said subject;
 b) forming a reaction mixture comprising nucleic acid amplification reagents, the test sample and at least one of the combinations of polynucleotides according to claim 1 or 3, said combination consisting of polynucleotide primers and at least one polynucleotide probe;
 c) subjecting said mixture to amplification conditions to generate at least one copy of said target nucleic acid sequence;
 d) hybridising the polynucleotide probe to the target nucleic acid sequence to form a probe:target hybrid;
 e) detecting the probe:target hybrid; and
 f) comparing the amount of probe:target hybrid to a standard, wherein comparing the amount of probe:target hybrid to a standard provides an indication of the amount of HBV nucleic acids present in the test sample.

In accordance with yet still another aspect of the present invention, there is provided a kit comprising at least one polynucleotide having a nucleic acid sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO:18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30, or the complement or homologues of said nucleic acid sequences, or a combination thereof.

BRIEF DESCRIPTION OF THE FIGURES

FIG. 1 illustrates the alignment of primers B, E, E2, H, Jr, Jf, K3, P, Rr, Rf and Br [SEQ ID NOs: 1, 3, 4, 5, 7, 8, 10, 11, 13, 14 and 16, respectively] and inner probe sequences C, I, K, Q and A [SEQ ID NOs: 2, 6, 9, 12 and 15, respectively] with the genome sequence of Hepatitis B virus (HBVAYWMCG; GenBank Accession No. X59795).

DETAILED DESCRIPTION OF THE INVENTION

The present invention provides polynucleotides wherein each polynucleotide can specifically hybridise to nucleic acids from all hepatitis B virus (HBV) genotypes.

Definitions

Unless defined otherwise, all technical and scientific terms used herein have the same meaning as commonly understood by one of ordinary skill in the art to which this invention pertains.

In the context of the present invention the term "polynucleotide" refers to a polymer of ribonucleic acid (RNA), deoxyribonucleic acid (DNA), modified RNA or DNA, or RNA or DNA mimetics. This term, therefore, includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

The term "specifically hybridise" as used herein refers to the ability of a nucleic acid to bind detectably and specifically to a second nucleic acid. Polynucleotides specifically hybridise to target nucleic acid strands under hybridisation and wash conditions that minimise appreciable amounts of detectable binding to non-specific nucleic acids. High stringency conditions can be used to achieve specific hybridisation conditions as known in the art. The skilled artisan will appreciate that some degree of mismatch or sequence overhang can be tolerated without departing from the spirit and scope of the present invention.

In accordance with the present invention, the polynucleotides specifically hybridise to a target nucleic acid sequence present in all HBV genomes. Thus, a "target sequence" as used herein comprises a nucleic acid sequence that is complementary to the nucleic acid sequence of one or more of the polynucleotides provided by the present invention. A target sequence in accordance with the present invention may be either single stranded or double stranded.

The polynucleotides according to the present invention are generally between about 7 and about 50 nucleotides in length. In one embodiment of the present invention, the polynucleotides are between about 10 and about 50 nucleotides in length. In related embodiments, the polynucleotides are between about 12 and about 35 nucleotides in length and between 16 and 27 nucleotides in length.

The polynucleotides according to the present invention have a melting temperature ($T_M$) in the range 45° C. to 80° C. In one embodiment of the present invention, the polynucleotides have a $T_M$ within the range 54° C. to 70° C. In accordance with the present invention, the polynucleotides specifically hybridise to a target HBV nucleic acid sequence without exhibiting significant hybridisation to non-HBV nucleic acids. In addition, the polynucleotides are selected such that they hybridise to conserved regions in the HBV genome, thus minimising mismatches with the target sequence, especially at the 3' end. This selection ensures that the polynucleotides are capable of hybridising to HBV nucleic acids from all genotypes and subtypes. Furthermore, the polynucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

As described above, the present invention provides polynucleotides which are HBV-specific but genotype-independent. As indicated previously, there are currently seven known genotypes of HBV, designated A–G. The polynucleotides described herein, therefore, can be used in the amplification and/or detection of nucleic acids from each of these genotypes of HBV. One skilled in the art will appreciate that new genotypes of HBV may be discovered or emerge in the future. The use of the polynucleotides to amplify and/or detect nucleic acids from new HBV genotypes is also considered to be within the scope of the present invention.

In one embodiment of the present invention, the polynucleotides comprise the nucleic acid sequences as set forth in SEQ ID NOs: 1–20, or the complement thereof. As is known in the art and as used herein, the complement of a polynucleotide refers to a nucleic acid sequence that is complementary to the polynucleotide but read in the reverse direction. Thus, the complement of SEQ ID NO: 1, given below in Table 1, is: 5'-AGAAGTCCACCACGAGTCTA-GACTCT-3'

TABLE 1

Polynucleotide Sequences

| Polynucleotide | Sequence | SEQ ID NO |
|---|---|---|
| B | 5'-AGAGTCTAGACTCGTGGTGGACTTCT-3' | 1 |
| Inner C | 5'-TGGCCAAAATTCGCAG-3' | 2 |
| E | 5'-AAGAAGATGAGGCATAGCAGCAGGATG-3' | 3 |
| E2 | 5'-TCCAGAAGAACCAACAAGAAGATGAGG-3' | 4 |
| H | 5'-GTGTGCACTTCGCTTCACCTCTG-3' | 5 |
| Inner I | 5'-AGTCCAAGAGTCCTCTTATG-3' | 6 |
| Jr | 5'-CAGACCAATTTATGCCTACAGCCTCC-3' | 7 |
| Jf | 5'-GAGGCTGTAGGCATAAATTGGT-3' | 8 |
| Inner K | 5'-AGCTTGGAGGCTTGAACAG-3' | 9 |
| K3 | 5'-GGAAAGAAGTCAGAAGGCAAAAA-3' | 10 |
| P | 5'-CCTCTGGGATTCTTTCCCGA-3' | 11 |
| Inner Q | 5'-CTGAGGGCTCCACCCCAA-3' | 12 |
| Rr | 5'-CACTGCATGGCCTGAGGAT-3' | 13 |
| Rf | 5'-TCATCCTCAGGCCATGCAGTGGAA-3' | 14 |
| Inner A | 5'-GAACTGGAGCCACCAGCA-3' | 15 |
| Br | 5'-CCCCTAGAAAATTGAGAGAAGTCCACC-3' | 16 |
| Inner C2 | 5'-GCCAAAATTCGCAGTCC-3' | 17 |
| Inner C3 | 5'-GGCCAAAATTCGCAGTCCC-3' | 18 |
| Inner C5 | 5'-CCAAAATTCGCAGTCC-3' | 19 |
| Inner C6 | 5'-CCAAAATTCGCAGTCCC-3' | 20 |

The nucleic acid sequences of the polynucleotides designated SEQ ID NOs: 1–9 and 11–20, listed in Table 1, are 100% identical to their target sequence in the HBVAYW-MCG genome (GenBank Accession No. X59795). However, it is understood in the art that a polynucleotide need not have 100% identity with its target sequence in order to specifically hybridise with that target. SEQ ID NO: 10, for example, specifically hybridises to its target sequence with which it has about 96% identity. A worker skilled in the art will appreciate that polynucleotides with even lower percent identity to their target sequence will retain their ability to specifically hybridise to this target.

The present invention, therefore, also contemplates polynucleotides that specifically hybridise to a target HBV nucleic acid sequence and comprise a nucleic acid sequence that is at least about 80% identical to any one of the nucleic acid sequences as set forth in SEQ ID NOs: 1–20. In one embodiment of the present invention, the polynucleotides specifically hybridise to a target HBV nucleic acid sequence and comprise a nucleic acid sequence that is at least about 90% identical to any one of the nucleic acid sequences as set forth in SEQ ID NOs: 1–20. In a related embodiment, the polynucleotides specifically hybridise to a target HBV nucleic acid sequence and comprise a nucleic acid sequence that is at least about 95% identical to any one of the nucleic acid sequences as set forth in SEQ ID NOs: 1–20. The percent identity between two nucleic acid sequences can be determined by a number of methods well-known in the art, for example, by using the BLASTN program of the University of Wisconsin Computer Group (GCG) software.

For the purposes of the present invention, polynucleotides as described above which specifically hybridise to a target HBV nucleic acid sequence and comprise a nucleic acid sequence that is at least about 80% identical to any one of the nucleic acid sequences as set forth in SEQ ID NOs: 1–20 are considered to be homologues of the polynucleotides of the present invention. The term "homologue," as used herein, thus includes polynucleotides comprising one of the nucleic acid sequences as set forth in SEQ ID NOs: 1–20 in which there are additions, deletions, and minor substitutions. For example, polynucleotides comprising one of the nucleic acid sequences as set forth in SEQ ID NOs: 1–20 in which nucleotides have been deleted from either the 3' or the 5' end, or from both ends, and which retain the ability to specifically hybridise to a target HBV nucleic acid sequence are considered to be homologues of the polynucleotides and, therefore, within the scope of the present invention.

Furthermore, polynucleotides which comprise one of the nucleic acid sequences as set forth in SEQ ID NOs: 1–20 and additional complementary or non-complementary nucleotides at either the 3' or the 5' end, or at both ends, which retain the ability to specifically hybridise to a target HBV nucleic acid sequence are also encompassed within the scope of the present invention. In one embodiment of the present invention, the polynucleotides comprise any one of the nucleic acid sequences as set forth in SEQ ID NOs: 2, 6, 9, 12, 15, 17–20 together with additional nucleotides at the 3' and 5' ends. In a related embodiment these polynucleotides have a nucleic acid sequence as set forth in any one of SEQ ID NOs: 21–30.

The present invention further contemplates polynucleotides that comprise any one of the nucleic acid sequences as set forth in SEQ ID NOs: 1–20, and homologues of these polynucleotides, in which one or more of the nucleotides has been replaced with a nucleotide analogue. In accordance with the present invention, incorporation of one or more nucleotide analogues into the polynucleotides is such that the analogue, or analogues, does not interfere with the ability of the polynucleotides to specifically hybridise to HBV nucleic acids.

Examples of polynucleotide analogues containing modifications or substitutions that are useful in the present invention include polynucleotides containing modified backbones or non-natural internucleoside linkages. In accordance with the present invention, modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl internucleoside linkages, mixed heteroatom and alkyl or cycloalkyl internucleoside linkages, or one or more short chain heteroatomic or heterocyclic internucleoside linkages. An example of such a non-phosphorus containing backbone is a morpholino linkage (see, for example, U.S. Pat. Nos. 5,185,444, 5,034,506, and 5,142,047). As is known in the art, modified polynucleotides may also contain one or more modified sugar moieties. For example, sugar moieties may be modified by substitution at the 2' position with a 2-methoxyethoxy (2-MOE) group (see, Martin et al., (1995) *Helv. Chim. Acta*, 78:486–504).

The present invention also contemplates analogues that are polynucleotide mimetics, in which both the sugar and the internucleoside linkage of the nucleotide units are replaced with novel groups. In these mimetics the base units are maintained for hybridisation with the target HBV nucleic acid sequence. An example of such a polynucleotide mimetic, which has been shown to have excellent hybridisation properties, is a peptide nucleic acid (PNA) (Nielsen et al., (1991) *Science*, 254:1497–1500; International Patent Application WO 92/20702). In PNA compounds, the sugar-backbone of the oligonucleotide is replaced with an amide containing backbone, in particular an aminoethylglycine backbone. The nucleobases are retained and are bound directly or indirectly to the aza-nitrogen atoms of the amide portion of the backbone.

The polynucleotides according to the present invention can be prepared by conventional techniques well-known to those skilled in the art. For example, the polynucleotides can be prepared using conventional solid-phase synthesis using commercially available equipment, such as that available from Applied Biosystems USA Inc. (Foster City, Calif.), DuPont, (Wilmington, Del.), or Milligen (Bedford, Mass.). Modified polynucleotides, such as phosphorothioates and alkylated derivatives, can also be readily prepared by similar methods known in the art.

Uses of the Polynucleotides

In the course of HBV infection, the presence of HBV nucleic acids in the serum precedes the appearance of known serological markers, which are detected by conventional immunoassays and provide the basis of current diagnostic tests. Detection of HBV nucleic acids in the serum or plasma of a subject, therefore, would provide a method of early diagnosis of HBV infection. The present invention provides HBV-specific, genotype-independent polynucleotides that can be used in assays to detect the presence of HBV nucleic acids in a test sample. In addition, when the polynucleotides according to the present invention are used in a quantitative assay format the quantity of HBV nucleic acids (i.e. the viral load) in a subject infected with HBV. Quantitation of HBV nucleic acids in an infected subject has particular relevance in assessing the degree to which the subject is responding to anti-viral therapy.

In accordance with the present invention, the polynucleotide sequences are designed such that they hybridise to nucleic acids from all known HBV genotypes, but do not exhibit significant hybridisation to non-HBV nucleic acids. As such, the polynucleotides of the present invention have a wide range of applications in a clinical or research setting. For example, the polynucleotides can be used as HBV-specific, genotype-independent primers to amplify HBV nucleic acid sequences, or as HBV-specific, genotype-independent probes to detect the presence of HBV nucleic acid sequences in a sample. The present invention further contemplates the use of a polynucleotide probe in combination with one or more polynucleotide primers for the amplification and subsequent detection of HBV nucleic acids in a sample. These methods are particularly useful for the detection of small quantities of HBV nucleic acids. Furthermore, the polynucleotides of the present invention can be used as genotype-independent primers and probes in assays to quantitate the amount of HBV nucleic acids in a sample.

i) Direct Detection of HBV Nucleic Acids

The polynucleotides according to the present invention can be employed directly as genotype-independent probes for the detection, or quantitation, or both, of HBV nucleic acids in a test sample. In essence, the test sample is contacted with at least one of the polynucleotides of the present invention under suitable hybridisation conditions and the hybridization between the target sequence and at least one of the polynucleotides is then detected by methods well-known in the art.

In the context of the present invention, a "test sample" is a sample suspected of containing, or known to contain, one or more target HBV nucleic acid sequences and in which one wants to determine the presence or absence and/or quantity of HBV nucleic acids. Typically, the test sample is derived from a biological source, for example, from blood or tissues such as liver tissue, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid and the like. The test sample can be used either directly as obtained from the source or following a pre-treatment to modify the character of the sample. Thus, the test sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, purifying nucleic acids, and the like. In one embodiment of the present invention, the test sample is a blood sample. In related embodiments, the test sample is serum or plasma.

For use as a HBV genotype-independent probe, the polynucleotides of the present invention may incorporate one or more detectable labels. Detectable labels are molecules or moieties a property or characteristic of which can be detected directly or indirectly and are chosen such that the ability of the polynucleotide to hybridise with its target sequence is not affected. Methods of labelling nucleic acid sequences are well-known in the art (see, for example, Ausubel et al., (1997 & updates) *Current Protocols in Molecular Biology*, Wiley & Sons, New York).

Labels suitable for use with the polynucleotides of the present invention include those that can be directly detected such as radioisotopes, fluorophores, chemiluminophores, enzymes, colloidal particles, fluorescent microparticles, intercalating dyes such as SYBR Green or ethidium bromide and the like. One skilled in the art will understand that directly detectable labels may require additional components, such as substrates, triggering reagents, light, and the like to enable detection of the label. The present invention also contemplates the use of labels that are detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the polynucleotide of the present invention, and the "conjugate" specifically binds to the specific binding member. Binding between the two members of the pair is typically chemical or physical in nature. Examples of such binding pairs include, but are not limited to, antigens and antibodies; avidin/streptavidin and biotin; haptens and antibodies specific for haptens; complementary nucleotide sequences; enzyme cofactors/substrates and enzymes; and the like.

The polynucleotides according to the present invention are also suitable for use as "capture probes" in sandwich-type assays. Capture probes and sandwich hybridisation assays are well-known in the art. Briefly, the polynucleotide capture probe is attached to a solid support and brought into contact with a test sample under suitable hybridisation conditions such that a probe:target hybrid is formed between the capture probe and any target nucleic acid present in the test sample. After one or more appropriate washing steps, the probe:target hybrid is detected, usually by means of a second "disclosure" probe or by a specific antibody that recognises the hybrid molecule. The use of the HBV-specific, genotype-independent polynucleotides as either a capture or disclosure probe, or both, in such sandwich hybridisation assays is thus considered to be within the scope of the present invention.

The present invention also contemplates the use of the polynucleotides in modified nucleic acid hybridisation assays. For example, U.S. Pat. No. 5,627,030 discloses a method to amplify the detection signal in a nucleic acid hybridisation assay. In the disclosed assay, a first polynucleotide probe sequence is hybridised under suitable conditions to a target sequence, the probe:target hybrid is subsequently immunocaptured and immobilised. A second polynucleotide probe which contains many repeating sequence units is then hybridised to the probe component of the probe:target hybrid. Detection is achieved by hybridisation of many labelled nucleic acid sequence probes, one to each of the repeating sequence units present in the second probe. The attachment of multiple labelled probes to the second probe thus amplifies the detection signal and increases the sensitivity of the assay. The use of the HBV-specific, genotype-independent polynucleotides in modified hybridisation assays of this type, either directly as a first probe, or as a second probe after modification to incorporate additional repeating sequence units by standard techniques, is thus considered to be within the scope of the present invention.

ii) Amplification of HBV Nucleic Acid Sequences

The polynucleotides according to the present invention can also be used as HBV-specific, genotype-independent primers for the amplification of HBV nucleic acids in a test sample. Amplification procedures are well-known in the art and include, but are not limited to, polymerase chain reaction (PCR), TMA, rolling circle amplification, nucleic acid sequence based amplification (NASBA), and strand displacement amplification (SDA). One skilled in the art will understand that for use in certain amplification techniques the primers may need to be modified, for example, for SDA the primer comprises additional nucleotides near its 5' end that constitute a recognition site for a restriction endonuclease. Similarly, for NASBA the primer comprises additional nucleotides near the 5' end that constitute an RNA polymerase promoter. Polynucleotides thus modified are considered to be within the scope of the present invention.

As is well-known in the art, certain criteria need to be taken into consideration when selecting a primer for an amplification reaction. For example, when a primer pair is required for the amplification reaction, the primers should be selected such that the likelihood of forming 3' duplexes is minimised, and such that the melting temperatures ($T_M$) are sufficiently similar to optimise annealing to the target sequence and minimise the amount of non-specific annealing. In this context, the polynucleotides according to the present invention are provided in combinations that can be used as primers in amplification reactions to specifically amplify HBV nucleic acid sequences. In one embodiment of the present invention, therefore, polynucleotides having the nucleic acids sequences as set forth in SEQ ID NOs: 1 and 3; SEQ ID NOs: 1 and 4; SEQ ID NOs: 5 and 7; SEQ ID NOs: 8 and 10, SEQ ID NOs: 11 and 13, SEQ ID NOs: 14 and 16, or the complement, homologues or analogues of these nucleic acid sequences, are provided together. In a related embodiment, these primer combinations are used to specifically amplify HBV nucleic acid sequences by PCR.

In accordance with the present invention, the method used to specifically amplify HBV nucleic acid sequences in a test sample generally comprises the steps of:
(a) forming a reaction mixture comprising nucleic acid amplification reagents, at least one polynucleotide primer and a test sample; and
(b) subjecting the mixture to amplification conditions to generate at least one copy of the target nucleic acid sequence, or a nucleic acid sequence complementary to the target sequence.

Appropriate amplification conditions required for step (b) can be readily determined by one skilled in the art. One skilled in the art will additionally understand that step (b) may be repeated several times using standard thermal cycling techniques in order to generate further copies of the target HBV nucleic acid sequence, or its complement.

The term "nucleic acid amplification reagents" includes conventional reagents employed in amplification reactions and includes, but is not limited to, one or more enzymes having polymerase activity, enzyme cofactors (such as magnesium or nicotinamide adenine dinucleotide (NAD)), salts, buffers, deoxynucleotide triphosphates (dNTPs; for example, deoxyadenosine triphosphate, deoxyguanosine triphosphate, deoxycytidine triphosphate and deoxythymidine triphosphate) and other reagents that modulate the activity of the polymerase enzyme or the specificity of the primers.

iii) Amplification and Detection of HBV Nucleic Acid Sequences

When detecting the presence of a small amount of target sequence in a sample, it is frequently necessary to first amplify the target sequence. This step ensures that the target sequences are present in sufficient number to allow detection of the hybridisation that takes place between the target and the probe polynucleotide. Use of the polynucleotides described herein in combinations that allow for the amplification and subsequent detection of target HBV nucleic acids is therefore contemplated by the present invention.

Specific amplicons produced by amplification of HBV nucleic acid sequences using the polynucleotides of the present invention, as described above, can be detected by a variety of methods known in the art. For example, one or more of the primers used in the amplification reactions may be labelled such that an amplicon can be directly detected by conventional techniques subsequent to the amplification reaction. Alternatively, a probe consisting of a labelled version of one of the primers used in the amplification reaction, or a third polynucleotide distinct from the primer sequences that has been labelled and is complementary to a region of the amplified sequence, can be added after the amplification reaction is complete. The mixture is then submitted to appropriate hybridisation and wash conditions and the label is detected by conventional methods.

The present invention also contemplates the use of the polynucleotides in modified amplification and detection assays. For example, U.S. Pat. No. 5,827,661 discloses a method of enhancing detection of nucleic acids amplified in a modified PCR reaction by subsequent RNA transcription of the amplicons, capture of the RNA transcripts by DNA probes and immuno-detection of the RNA:DNA hybrids. It will be readily apparent to one skilled in the art that the polynucleotides according to the present invention can be used directly as capture probes in these types of assays, or can be modified by standard techniques to include additional nucleotides at the 5' end which comprise an RNA polymerase promoter for use as primers in the modified PCR step as outlined above.

It will be readily appreciated that a procedure that allows both amplification and detection of target HBV nucleic acid sequences to take place concurrently in a single unopened reaction vessel would be advantageous. Such a procedure would avoid the risk of "carry-over" contamination in the post-amplification processing steps, and would also facilitate high-throughput assays and the adaptation of the procedure to automation. Furthermore, this type of procedure allows "real-time" monitoring of the amplification reaction as well as more conventional "end-point" detection.

The present invention thus includes the use of the polynucleotides in a method to specifically amplify and detect HBV nucleic acid sequences in a test sample in a single tube format. This may be achieved, for example, by including in the reaction vessel an intercalating dye such as SYBR Green or an antibody that specifically detects the amplified nucleic acid sequence. Alternatively a third polynucleotide distinct from the primer sequences, which is complementary to a region of the amplified sequence, may be included in the reaction.

Thus, in one embodiment of the present invention, the polynucleotides can be used in a method to specifically amplify and detect HBV nucleic acids in a test sample, which generally comprises the steps of:
(a) forming a reaction mixture comprising nucleic acid amplification reagents, at least one polynucleotide probe sequence, at least one polynucleotide primer and a test sample suspected of containing, or known to contain, one or more target HBV nucleic acid sequences;
(b) subjecting the mixture to amplification conditions to generate at least one copy of the target nucleic acid sequence, or a nucleic acid sequence complementary to the target sequence;

(c) hybridising the probe to the target nucleic acid sequence or the nucleic acid sequence complementary to the target sequence, so as to form a probe:target hybrid; and (d) detecting the probe:target hybrid as an indication of the presence of HBV nucleic acids in the sample.

One skilled in the art will understand that step (b) of the above method can be repeated several times prior to step (c) by thermal cycling the reaction mixture by techniques known in the art.

For use in an assay as described above, in which both amplification with polynucleotide primers and detection of target sequences using a polynucleotide probe occur concurrently in a single unopened reaction vessel, the polynucleotide probe needs to possess certain properties. For example, since the probe will be present during the amplification reaction, it should not interfere with the progress of this reaction and should also be stable under the reaction conditions. In addition, for real-time monitoring of reactions, the probe should be capable of binding its target sequence under the conditions of the amplification reaction and to emit a signal only upon binding this target sequence. Examples of probe molecules that are particularly well-suited to this type of procedure include molecular beacon probes and TaqMan® probes.

The present invention, therefore, contemplates the use of the polynucleotides as TaqMan® probes. As is known in the art, TaqMan® probes are dual-labelled fluorogenic nucleic acid probes composed of a polynucleotide complementary to the target sequence that is labelled at the 5' terminus with a fluorophore and at the 3' terminus with a quencher. TaqMan® probes are typically used as real-time probes in amplification reactions. In the free probe, the close proximity of the fluorophore and the quencher ensures that the fluorophore is internally quenched. During the extension phase of the amplification reaction, the probe is cleaved by the 5' nuclease activity of the polymerase and the fluorophore is released. The released fluorophore can then fluoresce and thus produces a detectable signal.

The present invention further contemplates the use of the polynucleotides as "molecular beacon" probes. Molecular beacon probes are well-known in the art, for example, see U.S. Pat. Nos. 6,150,097; 5,925,517 and 6,103,476. Basically, molecular beacons are polynucleotide probes capable of forming a stem-loop (hairpin) structure. The loop is a single-stranded structure containing sequences complementary to the target sequence, whereas the stem typically is unrelated to the target sequence and self-hybridises to form a double-stranded region. Nucleotides that are both complementary to the target sequence and that can self-hybridise may also form part of the stem region. Attached to one arm of the stem is a fluorophore moiety and to the other arm a quencher moiety. When the polynucleotide adopts a hairpin shape, the fluorophore and the quencher are in close proximity and the energy emitted by the fluorophore is thus absorbed by the quencher and given off as heat, resulting in internal quenching of the fluorophore. Upon binding of the polynucleotide to its target sequence, the fluorophore and the quencher become spatially separated and the fluorophore can fluoresce producing a detectable signal.

The present invention further contemplates the use of the HBV-specific, genotype-independent polynucleotides as linear probes in conjunction with a fluorophore and a high efficiency dark quencher, such as the Black Hole Quenchers (BHQ™; Biosearch Technologies, Inc., Novato, Calif.). As is known in the art, the high quenching efficiency and lack of native fluorescence of the BHQ™ dyes allows "random-coil" quenching to occur in linear probes labelled at one terminus with a fluorophore and at the other with a BHQ™ dye thus ensuring that the fluorophore does not fluoresce when the probe is in solution. Upon binding its target sequence, the probe stretches out, the fluorophore and quencher are thus spatially separated and the fluorophore fluoresces. One skilled in the art will appreciate that the BHQ™ dyes can also be used as the quencher moiety in molecular beacon or TaqMan® probes.

Suitable fluorophores and quenchers for use with the polynucleotides of the present invention can be readily determined by one skilled in the art (see also, Tgayi et al., *Nature Biotechnol.*, 16:49–53 (1998); Marras et al., *Genet. Anal.: Biomolec. Eng.*, 14:151–156 (1999)). Many fluorophores and quenchers are available commercially, for example from Molecular Probes (Eugene, Oreg.) or Biosearch Technologies, Inc. (Novato, Calif.). Examples of fluorophores that can be used in the present invention include, but are not limited to, fluorescein and fluorescein derivatives such as FAM, VIC, and JOE, 5-(2'-aminoethyl)aminonaphthalene-1-sulphonic acid (EDANS), coumarin and coumarin derivatives, Lucifer yellow, NED, Texas red, tetramethylrhodamine, tetrachloro-6-carboxyfluoroscein, 5-carboxyrhodamine, cyanine dyes and the like. Quenchers include, but are not limited to, DABCYL, 4'-(4-dimethylaminophenylazo)benzoic acid (DABSYL), 4-dimethylaminophenylazophenyl-4'-maleimide (DABMI), tetramethylrhodamine, carboxytetramethylrhodamine (TAMRA), BHQ™ dyes and the like. Methods of coupling fluorophores and quenchers to nucleic acids are well-known in the art.

In one embodiment of the present invention, the probes are molecular beacon probes. As is known in the art, certain criteria need to be met for a molecular beacon probe to be successful in monitoring or detecting an amplification reaction. The present invention, therefore, provides molecular beacon probes that comprise the polynucleotides of the present invention together with flanking self-complementary regions. The polynucleotides of the present invention, may make up the loop region of the molecular beacon, or they may make up the loop region and part of the stem region. Thus, the self-complementary stem sequences can be unrelated to the target sequence or may contain one or more nucleotides which are complementary to the target sequence.

In one embodiment of the present invention, polynucleotides having a nucleic acid sequence as set forth in any one of SEQ ID NOs: 2, 6, 9, 12, 15, 17, 18, 19 or 20, or the complement, homologues or analogues of these nucleic acid sequences, together with appropriate self-complementary flanking sequences are provided as molecular beacon probes. In a related embodiment, the molecular beacon probes have a nucleic acid sequence as set forth in any one of SEQ ID NOS: 21–30.

One skilled in the art will understand that the selection of primers to be used with the molecular beacon probe also requires certain criteria to be met. For example, it is important that there are no areas of complementarity that may cause the molecular beacon to bind to a primer, which would result in a high background signal.

The polynucleotides according to the present invention, therefore, are further provided in combinations, comprising two primers and at least one probe, that can be used to specifically amplify and detect HBV nucleic acid sequences in a test sample. In one embodiment of the present invention, polynucleotides comprising the nucleic acids sequences as set forth in SEQ ID NOs: 1, 2, and 3; SEQ ID NOs: 1, 2, and 4; SEQ ID NOs: 5, 6 and 7; SEQ ID NOs: 8, 9 and 10; SEQ ID NOs: 11, 12 and 13; SEQ ID NOs: 14, 15 and 16; SEQ ID NOs: 1, 3 and 17; SEQ ID NOs: 1, 3 and 18; SEQ ID NOs: 1, 3 and 19; SEQ ID NOs: 1, 3, and 20; SEQ ID NOs: 1, 4 and 17; SEQ ID NOs: 1, 4 and 18; SEQ ID NOs: 1, 4 and 19; SEQ ID NOs: 1, 4, and 20; SEQ ID NOs: 1, 3 and 21; SEQ ID NOs: 1, 3 and 26; SEQ ID NOs: 1, 3 and 27; SEQ ID NOs: 1, 3, and 28; SEQ ID NOs: 1, 3 and 29; SEQ ID NOs: 1, 3 and 30; SEQ ID NOs: 1, 4, and 21; SEQ ID NOs: 1, 4 and 26; SEQ ID NOs: 1, 4 and 27; SEQ ID NOs: 1, 4 and 28; SEQ ID NOs: 1, 4 and 29; SEQ ID NOs: 1, 4 and 30; SEQ ID NOs: 5, 7 and 22; SEQ ID NOs: 8, 10 and 23; SEQ ID NOs: 11, 13 and 24; SEQ ID NOs: 14, 16 and 25 or the complement, homologues or analogues of these nucleic acid sequences, are provided together. In a related embodiment, these combinations of polynucleotides are provided for the amplification and detection of HBV nucleic acid sequences by molecular beacon PCR.

As is known in the art, molecular beacon probes can be used to monitor the progress of an amplification reaction in real time. During the course of an amplification reaction, such as a PCR, the molecular beacon interacts with its target sequence at the annealing temperature for the probe, and a fluorescent signal is generated. As the number of target strands produced in the amplification reaction increases, the number of molecular beacons bound to their target increases concomitantly, as does the strength of the fluorescent signal.

In accordance with the present invention, therefore, the combinations of two primers and at least one probe, as described above, can be used in either end-point amplification and detection assays, in which the strength of the detectable signal is measured at the conclusion of the amplification reaction, or in real-time amplification and detection assays, in which the strength of the detectable signal is monitored throughout the course of the amplification reaction.

iv) Quantitation of HBV Nucleic Acids

The polynucleotides according to the present invention can also be used in assays to quantitate the amount of HBV nucleic acid present in a sample. Thus, the polynucleotides can be used as HBV-specific, genotype-independent primers and probes, as described above, in quantitative assays. Thus, the polynucleotides according to the present invention can be used in a method to specifically amplify, detect and quantitate HBV nucleic acid sequences in a test sample, which generally comprises the steps of:

(a) forming a reaction mixture comprising nucleic acid amplification reagents, at least one polynucleotide probe sequence that incorporates a label which produces a detectable signal upon hybridisation of the probe to its target sequence, at least one polynucleotide primer and a test sample that contains one or more target HBV nucleic acid sequences;

(b) subjecting the mixture to amplification conditions to generate at least one copy of the target nucleic acid sequence, or a nucleic acid sequence complementary to the target sequence;

(c) hybridising the probe to the target nucleic acid sequence or the nucleic acid sequence complementary to the target sequence, so as to form a probe:target hybrid;

(d) detecting the probe:target hybrid by detecting the signal produced by the hybridised labelled probe; and (e) comparing the amount of the signal produced to a standard as an indication of the amount of HBV nucleic acids present in the test sample.

One skilled in the art will understand that step (b) of the above method can be repeated several times prior to step (c) by thermal cycling the reaction mixture by standard techniques known in the art.

Various types of standards for quantitative assays are known in the art. For example, the standard can consist of a standard curve generated by amplification and detection of known quantities of HBV nucleic acids under the assay conditions. Alternatively, an internal standard can be included in the reaction. Such internal standards generally comprise a control target nucleic acid sequence and a control polynucleotide probe. The internal standard can further include an additional pair of primers. These control primers are unrelated to the polynucleotides of the present invention and are specific for the control target nucleic acid sequence.

In the context of the present invention, a control target nucleic acid sequence is a nucleic acid sequence that:

(a) can be amplified either by the HBV-specific primer or primer pair being used in a particular reaction or by the control primers;

(b) specifically hybridises to the control probe under suitable conditions; and (c) does not hybridise to an HBV-specific probe under the same conditions.

In the context of the present invention, in addition to fulfilling the standard requirements for probe molecules, the control polynucleotide probe for use in quantitation reactions:

(a) specifically hybridises to the control sequence under suitable conditions;

(b) does not hybridise to the target HBV sequence, to the HBV specific probe, or to the HBV-specific primers under the same conditions;

(c) incorporates a detectable label that is distinct from the label incorporated into the HBV-specific probe. The signals generated by these two labels when they bind their respective target sequences can thus be distinguished and quantified separately.

One skilled in the art will recognise that the actual nucleic acid sequence of the control target nucleic acid and the control probe is not important provided that they both meet the criteria outlined above. In one embodiment of the present invention, the control target nucleic acid comprises all or part of the nucleic acid sequence as set forth in SEQ ID NO: 32 and the control probe has a nucleic acid sequence as set forth in either SEQ ID NO: 33 or 34.

In the context of the present invention, the amount of HBV nucleic acid in a test sample can be quantified using "end point" methods or "real time" methods. One skilled in the art will appreciate that when used as HBV-specific probes in quantitative assays, the polynucleotides of the present invention can be conventional hybridisation probes, linear BHQ™ probes, TaqMan® probes, molecular beacon probes, or combinations or modified versions thereof. In one embodiment of the present invention, the polynucleotides are used as molecular beacon probes. In accordance with the present invention, quantitation of HBV nucleic acids using the polynucleotides in molecular beacon PCR provides a sensitivity equal to or better than 100 HBV copies per reaction.

The present invention provides polynucleotide primers and probes in combinations that can be used in quantitative reactions to amplify, detect and quantitate HBV nucleic acids in a test sample, such combinations comprising two primers and at least one probe. In one embodiment of the present invention, polynucleotides comprising the nucleic acids sequences as set forth in SEQ ID NOs: 1, 2, and 3; SEQ ID NOs: 1, 2, and 4; SEQ ID NOs: 5, 6 and 7; SEQ ID NOs: 8, 9 and 10; SEQ ID NOs: 11, 12 and 13; SEQ ID NOs: 14, 15 and 16; SEQ ID NOs: 1, 3 and 17; SEQ ID NOs: 1, 3 and 18; SEQ ID NOs: 1, 3 and 19; SEQ ID NOs: 1, 3, and 20; SEQ ID NOs: 1, 4 and 17; SEQ ID NOs: 1, 4 and 18; SEQ ID NOs: 1, 4 and 19; SEQ ID NOs: 1, 4, and 20; SEQ ID NOs: 1, 3 and 21; SEQ ID NOs: 1, 3 and 26; SEQ ID NOs: 1, 3 and 27; SEQ ID NOs: 1, 3, and 28; SEQ ID NOs: 1, 3 and 29; SEQ ID NOs: 1, 3 and 30; SEQ ID NOs: 1, 4, and 21; SEQ ID NOs: 1, 4 and 26; SEQ ID NOs: 1, 4 and 27; SEQ ID NOs: 1, 4 and 28; SEQ ID NOs: 1, 4 and 29; SEQ ID NOs: 1, 4 and 30; SEQ ID NOs: 5, 7 and 22; SEQ ID NOs: 8, 10 and 23; SEQ ID NOs: 11, 13 and 24; SEQ ID NOs: 14, 16 and 25 or the complement, homologues or analogues of these nucleic acid sequences, are provided together for use in a quantitative assay. In related embodiments, polynucleotides comprising nucleic acid sequences as set forth in SEQ ID NOs: 1, 3 and 26, or SEQ ID NOs: 1, 3 and 27 are provided together.

The present invention also contemplates the provision of any one of the above combinations of polynucleotides together with a control target nucleic acid sequence, which can be amplified by the specified primer pair, and a control polynucleotide probe for the quantitative reactions. In one embodiment of the present invention, the above combinations are provided together with SEQ ID NOs: 32 and 33 or SEQ ID NOs: 32 and 34. In a related embodiment the combination comprises polynucleotides comprising nucleic acid sequences as set forth in SEQ ID NOs: 1, 3, 26, 32 and 33, or SEQ ID NOs: 1, 3, 27, 32 and 34. The present invention further provides for the inclusion of control primers, which specifically amplify the control target nucleic acid sequence, in the quantitative reactions.

High-Throughput Assays

The amplification and/or detection methods in which the polynucleotides according to the present invention can be employed are suitable for adaptation as high-throughput assays. High-throughput assays provide the advantage of processing many samples simultaneously and significantly decrease the time required to screen a large number of samples. The present invention, therefore, contemplates the use of the polynucleotides of the present invention in high-throughput screening or assays to detect and/or quantitate HBV nucleic acids in a plurality of test samples.

For high-throughput assays, reaction components are usually housed in a multi-container carrier or platform, such as a multi-well microtiter plate, which allows a plurality of assays each containing a different test sample to be monitored simultaneously. The present invention also contemplates highly automated high-throughput assays to increase the efficiency of the screening or assay process. Many high-throughput screening or assay systems are now available commercially, as are automation capabilities for many procedures such as sample and reagent pipetting, liquid dispensing, timed incubations, formatting samples into microarrays, microplate thermocycling and microplate readings in an appropriate detector, resulting in much faster throughput times.

Kits

The polynucleotides in accordance with the present invention can be provided as part of a kit that allows for the genotype-independent detection and/or quantitation of HBV nucleic acids. Such kits comprise one or more of the HBV-specific, genotype-independent polynucleotides for use as a primer and/or probe. In one embodiment of the present invention, the polynucleotides are provided in the kits in combinations for use as primers to specifically amplify HBV nucleic acids in a test sample. In a related embodiment, the polynucleotides are provided in combinations that comprise the nucleic acid sequences as set forth in SEQ ID NOs: 1 and 3; SEQ ID NOs: 1 and 4; SEQ ID NOs: 5 and 7; SEQ ID NOs: 8 and 10, SEQ ID NOs: 11 and 13, SEQ ID NOs: 14 and 16, or the complement, homologues or analogues of these nucleic acid sequences.

In another embodiment, the polynucleotides are provided in the kits in combinations comprising two primers and at least one probe. In a related embodiment, the polynucleotides are provided in combinations that comprise the nucleic acid sequences as set forth in SEQ ID NOs: 1, 2, and 3; SEQ ID NOs: 1, 2, and 4; SEQ ID NOs: 5, 6 and 7; SEQ ID NOs: 8, 9 and 10; SEQ ID NOs: 11, 12 and 13; SEQ ID NOs: 14, 15 and 16; SEQ ID NOs: 1, 3 and 17; SEQ ID NOs: 1, 3 and 18; SEQ ID NOs: 1, 3 and 19; SEQ ID NOs: 1, 3, and 20; SEQ ID NOs: 1, 4 and 17; SEQ ID NOs: 1, 4 and 18; SEQ ID NOs: 1, 4 and 19; SEQ ID NOs: 1, 4, and 20; SEQ ID NOs: 1, 3 and 21; SEQ ID NOs: 1, 3 and 26; SEQ ID NOs: 1, 3 and 27; SEQ ID NOs: 1, 3, and 28; SEQ ID NOs: 1, 3 and 29; SEQ ID NOs: 1, 3 and 30; SEQ ID NOs: 1, 4, and 21; SEQ ID NOs: 1, 4 and 26; SEQ ID NOs: 1,4 and 27; SEQ ID NOs: 1, 4 and 28; SEQ ID NOs: 1, 4 and 29; SEQ ID NOs: 1, 4 and 30; SEQ ID NOs: 5, 7 and 22; SEQ ID NOs: 8, 10 and 23; SEQ ID NOs: 11, 13 and 24; SEQ ID NOs: 14, 16 and 25, or the complement, homologues or analogues of these nucleic acid sequences.

Kits for the quantitation of HBV nucleic acids may additionally contain a control target nucleic acid and a control polynucleotide probe. Thus, in one embodiment of the present invention, the kits comprise one of the above combinations of polynucleotides comprising two primers and at least one probe, together with a control target nucleic acid sequence, which can be amplified by the specified primer pair, and a control polynucleotide probe. In a related embodiment of the present invention, the control target nucleic acid sequence comprises the nucleic acid sequences as set forth in SEQ ID NO: 32 and the control probes comprises the nucleic acid sequence as set forth in either SEQ ID NO: 33 or 34. In other related embodiments, the combination of polynucleotides and control target sequence and control probe consists of polynucleotides comprising nucleic acid sequences as set forth in SEQ ID NOs: 1, 3, 26, 32 and 33, or in SEQ ID NOs: 1, 3, 27, 32 and 34. The present invention further provides kits that include control primers, which specifically amplify the control target nucleic acid sequence.

The kits can optionally include amplification reagents, reaction components and/or reaction vessels. One or more of the polynucleotides provided in the kit can incorporate a detectable label, or the kit may include reagents for labelling the polynucleotides. One or more of the components of the kit may be lyophilised and the kit may further comprise reagents suitable for the reconstitution of the lyophilised components. The kit can additionally contain instructions for use.

Applications

The polynucleotides according to the present invention can find application in clinical or research settings for the genotype-independent detection and/or quantitation of HBV nucleic acids. Thus, in these settings the polynucleotides can be used in assays to diagnose HBV infection in a subject, or to monitor the HBV viral load in a subject infected with HBV. Monitoring the viral load in a subject is particularly important in identifying or monitoring response to anti-viral therapy.

To gain a better understanding of the invention described herein, the following examples are set forth. It should be understood that these examples are for illustrative purposes only. Therefore, they should not limit the scope of this invention in any way.

EXAMPLES

TABLE 2

Molecular Beacon Probe Sequences and Appropriate Primer Pairs for Molecular Beacon PCR

| Probe | Sequence[1] | SEQ ID NO | Primer Pair |
|---|---|---|---|
| C | 5'-ccgagTGGCCAAAATTCGCAGctcgg-3' | 21 | B + E |
|   |   |   | B + E2 |
| I | 5'-ctgcgAGTCCAAGAGTCCTCTTATGcgcag-3' | 22 | H + Jr |
| K | 5'-cgcttAGCTTGGAGGCTTGAACAGaagcg-3' | 23 | Jf + K3 |
| Q | 5'-cgcagCTGAGGGCTCCACCCCAActgcg-3' | 24 | P + Rr |
| A | 5'-cgctcGAACTGGAGCCACCAGCAgagcg-3' | 25 | Rf + Br |
| C2 | 5'-ccgaGCCAAAATTCGCAGTCCtcgg-3' | 26 | B + E |
|   |   |   | B + E2 |
| C3 | 5'-ccgaGGCCAAAATTCGCAGTCCCtcgg-3' | 27 | B + E |
|   |   |   | B + E2 |
| C4 | 5'-cgaGGCCAAAATTCGCAGTCCCtcg-3' | 28 | B + E |
|   |   |   | B + E2 |
| C5 | 5'-ccgatCCAAAATTCGCAGTCCatcgg-3' | 29 | B + E |
|   |   |   | B + E2 |
| C6 | 5'-cgaccaaCCAAAATTCGCAGTCCCggtcg-3' | 30 | B + E |
|   |   |   | B + E2 |

[1]Sequences complementary to the HBV sequence are indicated in capitals. Sequences that are self-complementary and form the stem of the beacon probe are underlined (note that in some instances nucleotides complementary to HBV also form part of the self-complementary stem)..
In probe C6 two "junk" bases are included which do not participate in hybridization with either HBV or with the stem sequence and are indicated in italics. OR-- In probe C6 two "junk" bases (indicated in italics) are included which are not complementary to HBV or stem sequences.

TABLE 3

Control Target Nucleic Acid and Beacon Probe Sequences

| Probe/Target | Sequence | SEQ ID NO |
|---|---|---|
| Target | 5'-TTTGCTCACATGTTCTTTCCTGCGTTATCCCCTGAWTCTG TGGATAACCGTATTACCGCCTTTGAGTGAGCTGATACCGCT CGCCGCAGCCGAACGACCGAGCGCAGCGAGTCAGTGAGCG AGGAAGCGGAAGAGCGCCCAATACGCAAACCGCCTCTCCC CGCGCGTTGGCCGATTCATTAATGCAGGTTAACCTGGCTTAT CGAAATTAATACGACTCACTATAGGGAGACCGGCAGATCTG ATATCATCGATGAATTCAGAGTCTAGACTCGTGGTGGACTT CTTGGAGCTGGTCGTATTGGATCTGCTTATGCAAGAATGAT GGTAGAAGGGTTTAAGATGAACCTGATCTACTTTGATCTTTA TCAGTCAACCAGGCTCGAAAAGTTCGTTACAGCCTATGGCG AGTTCCTAAAAGCCAACGGTGAGGTTCCATCCTGCTGCTAT GCCTCATCTTCTTGTCGACCTGCAGGCATGCAAGCTTCAGCT GCTCGAGTTCTATAGTGTCACCTAAATCGTATGTGTATGATA CATAAGGTTATGTATTAATTGTAGCCGCGTTCTAACGACAAT ATGTCCATATGGTGCACTCTCAGTACAATCTGCTCTGATGCC GCATAGTTAAGCCAGCCCCGACACCCGCCAACACCCGCTGA CGCGCCCTGACGGGCTTGTCTGCTCCCGGCATCCGCTTACA GACAAGCTGTGACCGTCTCCGGGAGCTGCATGTGTCAGAGG TTTTCACCGTCATCACCGAAACGCGCGAGACGAAAGGGCCT CGTGATACGCCTATTTTTATAGGT-3' | 31 |
| Target | 5'-AGAGTCTAGACTCGTGGTGGACTTCTTGGAGCTG GTCGTATTGGATCTGCTTATGCAAGAATGATGGTAGAAGGG TTTAAGATGAACCTGATCTACTTTGATCTTTATCAGTCAACC AGGCTCGAAAAGTTCGTTACAGCCTATGGCGAGTTCCTAAA AGCCAACGGTGAGGTTCCATCCTGCTGCTATGCCTCATCTTC TT-3' | 32 |
| Bic26 | 5'-CGCGACTTTGATCTTTATCAGTCAACCAGGCTCGCG-3' | 33 |
| Bic26b | 5'-CGACCTTTGATCTTTATCAGTCAACCAGGTCG-3' | 34 |

Example 1

Molecular Beacon PCR for the Detection of HBV Nucleic Acids

The following polynucleotides were used as primers and probes in molecular beacon PCR.

Primer/Probe Set BCE
Forward Primer (B): SEQ ID NO: 1
Beacon Probe (C): SEQ ID NO: 21
Reverse primer (E): SEQ ID NO: 3

Primer/Probe Set BCE2
Forward Primer (B): SEQ ID NO: 1
Beacon Probe (C): SEQ ID NO: 21
Reverse primer (E2): SEQ ID NO: 4

Primer/Probe Set HIJ
Forward Primer (H): SEQ ID NO: 5
Beacon Probe (I): SEQ ID NO: 22
Reverse primer (Jr): SEQ ID NO: 7

Primer/Probe Set JKK3
Forward Primer (Jf): SEQ ID NO: 8
Beacon Probe (K): SEQ ID NO: 23
Reverse primer (K3): SEQ ID NO: 10

Each of the probe sequences contains a fluorophore moiety (FAM) and a quencher moiety (DABCYL) at the 5' and 3' ends, respectively.

Experimental Conditions

1. Reactions were assembled in 100 μl total volume containing the following:
   a. 1×PCR Buffer II (Applied Biosystems, Foster City, Calif.)
   b. 3.5 mM $MgCl_2$
   c. 0.4 mM dNTPs
   d. Forward Primer
   e. Reverse Primer
   f. HBV Beacon Probe (FAM-DABCYL)
   g. 7 units Amplitaq Gold polymerase (Applied Biosystems)
   h. Sample/standard to be tested Conditions for Set BCE:
   Primer B at 150 nM, Beacon Probe C at 100 nM, Primer E at 450 nM per reaction.
   Conditions for Set HIJ:
   Primer H at 300 nM, Beacon Probe I at 50 nM, Primer J at 150 nM per reaction.
   Conditions for Set BCE2:
   Primer B at 150 nM, Beacon Probe C at 75 nM, Primer E2 at 450 nM per reaction.
   Conditions for Set JKK3:
   Primer J at 450 nM, Beacon Probe K at 50 nM, Primer K3 at 150 nM per reaction.

2. The following HBV Standards were run:
   a. Negative (0 copies HBV DNA), 3 replicates
   b. 10 copies HBV DNA, 3 replicates
   c. 100 copies HBV DNA, 3 replicates
   d. 1E4 copies HBV DNA, 3 replicates
   e. 1E5 copies HBV DNA, 3 replicates
   f. 1E6 copies HBV DNA, 2 replicates 3. The PCR reactions were run on a 96-well GeneAmp® PCR System 9700 thermal cycler (Applied Biosystems). Briefly, the PCR reaction was subjected to 10 minutes of incubation at 94° C., followed by 45 cycles of heating and cooling between 94° C. for 1 minute and 58° C. for 1 minute. After the completion of the 45 cycles, the reactions were incubated for 10 additional minutes at 58° C., followed by heat denaturation for 5 minutes at 94° C. Next, the beacon probe was hybridised to one strand of the amplicon by lowering the temperature of the reaction in stages, first at 55° C. for 15 minutes, then 25° C. for 15 minutes and finally 4° C. until the plate is read on a fluorescence plate reader.

4. After thermal cycling, the plate was read on a Cytofluor Series 4000 Fluorescence Multi-Well plate reader (Perseptive Biosystems, Framingham, Mass.) at ambient room temperature to determine FAM fluorescence signal in each reaction. Results are given in Tables 4 and 5.

TABLE 4

Fluorescence Readings for Various Primer/Probe Sets used in Molecular Beacon PCR

| Copies of HBV Target | Fluorescence Reading (FAM signal ± SD) | | | |
|---|---|---|---|---|
| | Primer/Probe Set BCE | Primer/Probe Set BCE2 | Primer/Probe Set HIJ | Primer/Probe Set JKK3 |
| 0 | 10554 ± 515 | 4880 ± 265 | 6947 ± 202 | 3949 ± 149 |
| 10 | 18025 ± 1868 | 9682 ± 373 | 24882 ± 788 | 7103 ± 2186 |
| 100 | 31144 ± 1221 | 10848 ± 239 | 32547 ± 797 | 9651 ± 136 |
| 10000 | 61045 ± 1893 | 16277 ± 1182 | 44563 ± 1065 | 11581 ± 867 |
| 100000 | 70727 ± 2475 | 19630 ± 621 | 42719 ± 651 | 11726 ± 476 |
| 1000000 | 78086 ± 828 | 21106 ± 363 | 40653 ± 243 | 12290 ± 530 |

TABLE 5

Signal to Noise Ratios for Fluorescence Readings for Various Primer/Probe Sets used in Molecular Beacon PCR

| Copies of HBV Target | Signal to Noise Ratio | | | |
|---|---|---|---|---|
| | Primer/Probe Set BCE | Primer/Probe Set BCE2 | Primer/Probe Set HIJ | Primer/Probe Set JKK3 |
| 0 | 1.00 | 1.00 | 1.00 | 1.00 |
| 10 | 1.71 | 1.98 | 3.58 | 1.80 |
| 100 | 2.95 | 2.22 | 4.68 | 2.44 |
| 10 000 | 5.78 | 3.34 | 6.41 | 2.93 |
| 100 000 | 6.70 | 4.02 | 6.15 | 2.97 |
| 1 000 000 | 7.40 | 4.33 | 5.85 | 3.11 |

Example 2

Quantitative Assay for HBV Nucleic Acids—Endpoint Format

Protocol:
1. An HBV Genotype Panel (Millennium Biotech, Ft. Lauderdale, Fla.) containing plasma samples of HBV Genotypes A through F was prepared using the QIAamp DNA Blood Mini kit (Qiagen Inc., Valencia, Calif.).
2. Reactions were assembled in 10 μl total volume containing the following:
   a. 1×Amplitaq Gold Buffer (Applied Biosystems, Foster City, Calif.)
   b. 3.5 mM $MgCl_2$
   c. 0.4 mM dNTPs
   d. 0.15 μM Forward Primer B (SEQ ID NO: 1)
   e. 0.45 μM Reverse Primer E (SEQ ID NO: 3)
   f. 0.1 μM Beacon Probe C2 FAM-DABCYL (SEQ ID NO: 26)
   g. 0.1 μM Control Probe Bic26b Texas Red-DABCYL (SEQ ID NO: 34)
   h. 300 copies Internal Control (SEQ ID NO: 32)
   i. 8 Units Amplitaq Gold (Applied Biosystems)
   j. Sample to be tested.
3. In addition to the genotype samples, the following set of HBV Standards was run:
   a. Negative, (0 copies HBV DNA), 4 replicates
   b. 10 copies HBV DNA, 8 replicates
   c. $10^2$ copies HBV DNA, 8 replicates
   d. $10^3$ copies HBV DNA, 4 replicates
   e. $10^4$ copies HBV DNA, 4 replicates
   f. $10^5$ copies HBV DNA, 8 replicates
   g. $10^6$ copies HBV DNA, 4 replicates
4. The PCR reactions were run on a 96-well GeneAmp® PCR System 9700 thermal cycler (Applied Biosystems) and the fluorescent signal from the hybridised beacon probes was measured on an FLx800 microplate fluorescence reader (Biotek Instruments, Winooski, Vt.). The genotype samples are labelled S1 through S15, and the standards are labelled Neg, 10, 100, 1E3, 1E4, lES, and 1E6.

The cycling parameters set for the thermal cycler are described as follows: 10 minutes of incubation at 94° C., followed by 45 cycles of heating and cooling between 92° C. for 30 seconds and 60° C. for 1 minute. After the completion of the 45 cycles, the amplicons were incubated for 10 additional minutes at 68° C., followed by heat denaturation for 5 minutes at 94° C. Next, each beacon probe (C2 Fam-Dabcyl and Bic26b Texas Red-Dabcyl) were hybridized to one strand of its specific amplicon (HBV or Internal Control) by lowering the temperature of the reaction in stages, first at 55° C. for 15 minutes, then 25° C. for 15 minutes and finally 4° C. until the plate is read on a fluorescence plate reader.

After thermal cycling, the plate was read on a Biotek FLx800 reader at ambient room temperature to determine FAM and Texas Red (TR) fluorescence in each well.

5. The FAM fluorescence signal and TR fluorescence signal for each well were divided, and the Log (base 10) of that number was taken. This number [log(FAM/TR)] is called the Log Fluorescence Ratio (LFR). The log copy per reaction was plotted vs. LFR reaction for the standards run.
6. The quantity of each sample was determined from the standard curve by the linear equation y=mx+b, where y is the log fluorescence ratio of the unknown sample, m is the slope of the standard curve (from log 1 to log 6), x is the log copies of HBV in the reaction, and b is the y-intercept of the standard curve (from log 1 to log 6).
7. The summary data for the HBV genotype samples is shown in Table 6 (below).

TABLE 6

Slope from line equation = 0.3074
y-intercept = −0.8654
Summary Data for HBV Genotype Samples S1–S15
(Endpoint Assay Format)

| Sample | Sample ID | Geno-type | Sero-type | Log Copies/ Reaction | Copies/ Reaction | Comments |
|---|---|---|---|---|---|---|
| S1 | 11160 | A | adw2 | 6.26 | 1834427 | >ULQ[1] |
| S2 | 13621 | A | adw2 | 2.33 | 212 | |
| S3 | 13643 | A | adw2 | 1.06 | 11 | |
| S4 | 11157 | B | adw2 | 4.77 | 58490 | Inhibited sample |
| S5 | 13373 | B | adw2 | 2.55 | 359 | |
| S6 | 11159 | C | adr | 4.34 | 22089 | Inhibited sample |
| S7 | 13619 | C | adr | 1.77 | 59 | |
| S8 | 13620 | C | adr | 6.39 | 2475258 | >ULQ[1] |
| S9 | 13617 | D | ayw2 | 1.09 | 12 | |
| S10 | 13618 | D | ayw2 | 2.10 | 126 | |
| S11 | 13622 | D | ayw2 | 6.33 | 2130895 | >ULQ[1] |
| S12 | 7870 | E | ayw4 | 3.21 | 1605 | |
| S13 | 7875 | E | ayw4 | 3.04 | 1104 | |

TABLE 6-continued

Slope from line equation = 0.3074
y-intercept = −0.8654
Summary Data for HBV Genotype Samples S1–S15
(Endpoint Assay Format)

| Sample | Sample ID | Genotype | Serotype | Log Copies/ Reaction | Copies/ Reaction | Comments |
|---|---|---|---|---|---|---|
| S14 | 12466 | F | adw4 | 2.78 | 606 | |
| S15 | 12469 | F | adw4 | 6.33 | 2130895 | >ULQ[1] |

[1]ULQ denotes that the sample has an HBV viral load above the upper limit of quantitation for this assay format.

Example 3

Quantitative Assay for HBV Nucleic Acids—Real Time Format

Protocol:
1. An HBV Genotype Panel (Millennium Biotech, Ft. Lauderdale, Fla.) containing plasma samples of HBV Genotypes A through F was prepared using the QIAamp DNA Blood Mini kit (Qiagen Inc., Valencia, Calif.). The panel members are denoted below as U1 to U15.
2. Reactions were assembled in 100l total volume containing the following:
   a. 1×Amplitaq Gold Buffer (Applied Biosystems, Foster City, Calif.)
   b. 3.5 mM $MgCl_2$
   c. 0.4 mM dNTPs
   d. 0.45 µM Forward Primer B (SEQ ID NO: 1)
   e. 0.45 µM Reverse Primer E (SEQ ID NO: 3)
   f. 0.2 µM Beacon Probe C3 FAM-DABCYL (SEQ ID NO: 27)
   g. 0.2 µM Control Probe Bic26 Texas Red-DABCYL (SEQ ID NO: 33)
   h. 500 copies Internal Control (SEQ ID NO: 32)
   i. 10 Units Amplitaq Gold (Applied Biosystems)
   j. Sample to be tested.
3. In addition to the genotype samples, duplicate runs of the following HBV Standards were run:
   a. No Template Control (NTC)
   b. 10 copies HBV DNA
   c. $10^2$ copies HBV DNA
   d. $10^3$ copies HBV DNA
   e. $10^4$ copies HBV DNA
   f. $10^5$ copies HBV DNA
   g. $10^6$ copies HBV DNA
   h. $10^7$ copies HBV DNA
   i. $10^8$ copies HBV DNA
   j. $10^9$ copies HBV DNA The standards and samples were run on an Mx4000™ Multiplex Quantitative PCR System (Stratagene, La Jolla, Calif.).
4. The cycling parameters set for the thermal cycler are described as follows: 10 minutes of incubation at 95° C., followed by 45 cycles of heating and cooling between 95° C. for 30 seconds and 50° C. for 1 minute. Note that at the anneal temperature (50° C.); a fluorescence reading was taken at each cycle repetition.
5. The Mx4000 software plots cycle repetition number vs. fluorescence. The software sets a threshold fluorescence value such that a noticeable increase in signal is occurring, signifying that the amplification is in exponential phase. The cycle repetition number at which a sample crosses this threshold is known as $C_t$.
6. The software draws a standard curve by plotting log (copies HBV) v. $C_t$. Using linear regression; the unknown samples are then quantitated from the standard curve.
7. The data used to draw the standard curve and to quantitate the samples is shown in Table 7 (below).

TABLE 7

Data for Standard Curve and Quantitation of HBV Unknown Samples U1–U15 (Real Time Assay Format)

| Sample | Sample ID | Genotype | Serotype | $C_t$ | Final Call | Quantity/ Reaction |
|---|---|---|---|---|---|---|
| NTC | | | | No Ct | − | 0 |
| NTC | | | | No Ct | − | 0 |
| Standard | | | | 36.5 | + | 1.00E+01 |
| Standard | | | | 37.05 | + | 1.00E+01 |
| Standard | | | | 33.54 | + | 1.00E+02 |
| Standard | | | | 33.42 | + | 1.00E+02 |
| Standard | | | | 30.46 | + | 1.00E+03 |
| Standard | | | | 30.28 | + | 1.00E+03 |
| Standard | | | | 27.13 | + | 1.00E+04 |
| Standard | | | | 27.21 | + | 1.00E+04 |
| Standard | | | | 23.69 | + | 1.00E+05 |
| Standard | | | | 23.67 | + | 1.00E+05 |
| Standard | | | | 20.36 | + | 1.00E+06 |
| Standard | | | | 20.4 | + | 1.00E+06 |
| Standard | | | | 16.93 | + | 1.00E+07 |
| Standard | | | | 17.03 | + | 1.00E+07 |
| Standard | | | | 13.43 | + | 1.00E+08 |
| Standard | | | | 13.38 | + | 1.00E+08 |
| Standard | | | | 10.08 | + | 1.00E+09 |
| Standard | | | | 10.09 | + | 1.00E+09 |
| U1 | 11160 | A | adw2 | 16.86 | + | 1.03E+07 |
| U2 | 13621 | A | adw2 | 32.58 | + | 2.05E+02 |
| U3 | 13643 | A | adw2 | 36.9 | + | 1.04E+01 |
| U4 | 11157 | B | adw2 | 27.4 | + | 7.27E+03 |
| U5 | 13373 | B | adw2 | 31.64 | + | 3.90E+02 |
| U6 | 11159 | C | adr | 15.76 | + | 2.21E+07 |
| U7 | 13619 | C | adr | 34.9 | + | 4.14E+01 |
| U8 | 13620 | C | adr | 15.02 | + | 3.68E+07 |
| U9 | 13617 | D | ayw2 | 39.64 | + | 1.59 |
| U10 | 13618 | D | ayw2 | 33.14 | + | 1.39E+02 |
| U11 | 13622 | D | ayw2 | 14.66 | + | 4.69E+07 |
| U12 | 7870 | E | ayw4 | 30.8 | + | 6.97E+02 |
| U13 | 7875 | E | ayw4 | 31.36 | + | 4.74E+02 |
| U14 | 12466 | F | adw4 | 31.86 | + | 3.35E+02 |
| U15 | 12469 | F | adw4 | 14.11 | + | 6.87E+07 |

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A composition comprising a forward primer and a reverse primer, wherein the forward primer consists of SEQ ID NO: 1 and the reverse primer consists of SEQ ID NO: 3, and wherein the primers can be used to detect hepatitis B virus (HBV).

2. The composition of claim 1 further comprising an isolated nucleic acid sequence selected from the group consisting of SEQ ID NO: 2, SEQ ID NO: 17, SEQ ID NO: 21, SEQ ID NO: 26 and SEQ ID NO: 28.

3. The composition of claim 1 further comprising an isolated nucleic acid sequence as set forth in SEQ ID NO: 27.

4. A kit for the amplification of nucleic acid sequences comprising a forward primer and a reverse primer, wherein the forward primer consists of SEQ ID NO: 1 and the reverse primer consists of SEQ ID NO: 3, and wherein the primers can be used to detect hepatitis B virus (HBV).

5. A kit for the amplification of nucleic acid sequences of claim 4 further comprising an isolated nucleic acid sequence selected from the group consisting of SEQ ID NO: 2, SEQ ID NO: 17, SEQ ID NO: 21, SEQ ID NO: 26 and SEQ ID NO: 28.

6. A kit for the amplification of nucleic acid sequences of claim 4 further comprising an isolated nucleic acid sequence as set forth in SEQ ID NO: 27.

7. A method for detecting Hepatitis B virus (HBV) in a test sample suspected of containing or known to contain one or more target HBV nucleic acid sequences comprising:
   a) contacting said test sample with the forward and reverse primers of claim 1 under hybridizing conditions;
   b) amplifying nucleic acid sequence or sequences that may be present in the test sample; and
   c) detecting the amplification of one or more target HBV nucleic acid sequences, wherein a positive detection of a target HBV nucleic acid sequence is indicative of the presence of HBV in the test sample.

* * * * *

SEQUENCE LISTING

<160> NUMBER OF SEQ ID NOS: 34

<210> SEQ ID NO 1
<211> LENGTH: 26
<212> TYPE: DNA
<213> ORGANISM: Artificial Sequence
<220> FEATURE:
<223> OTHER INFORMATION: Forward Primer B

<400> SEQUENCE: 1
agagtctaga ctcgtggtgg acttct                                            26

<210> SEQ ID NO 2
<211> LENGTH: 16
<212> TYPE: DNA
<213> ORGANISM: Artificial Sequence
<220> FEATURE:
<223> OTHER INFORMATION: Inner Probe C

<400> SEQUENCE: 2
tggccaaaat tcgcag                                                       16

<210> SEQ ID NO 3
<211> LENGTH: 27
<212> TYPE: DNA
<213> ORGANISM: Artificial Sequence
<220> FEATURE:
<223> OTHER INFORMATION: Reverse Primer E

<400> SEQUENCE: 3
aagaagatga ggcatagcag caggatg                                           27

<210> SEQ ID NO 4
<211> LENGTH: 27
<212> TYPE: DNA
<213> ORGANISM: Artificial Sequence
<220> FEATURE:
<223> OTHER INFORMATION: Primer E2

<400> SEQUENCE: 4
tccagaagaa ccaacaagaa gatgagg                                           27

<210> SEQ ID NO 5
<211> LENGTH: 23
<212> TYPE: DNA
<213> ORGANISM: Artificial Sequence
<220> FEATURE:
<223> OTHER INFORMATION: Forward Primer H

<400> SEQUENCE: 5
gtgtgcactt cgcttcacct ctg                                               23

<210> SEQ ID NO 6
<211> LENGTH: 20
<212> TYPE: DNA
<213> ORGANISM: Artificial Sequence
<220> FEATURE:
<223> OTHER INFORMATION: Inner Probe I

<400> SEQUENCE: 6
agtccaagag tcctcttatg                                                   20

<210> SEQ ID NO 7
<211> LENGTH: 26

```
<212> TYPE: DNA
<213> ORGANISM: Artificial Sequence
<220> FEATURE:
<223> OTHER INFORMATION: Reverse Primer Jr

<400> SEQUENCE: 7
cagaccaatt tatgcctaca gcctcc                                          26

<210> SEQ ID NO 8
<211> LENGTH: 22
<212> TYPE: DNA
<213> ORGANISM: Artificial Sequence
<220> FEATURE:
<223> OTHER INFORMATION: Forward Primer Jf

<400> SEQUENCE: 8
gaggctgtag gcataaattg gt                                              22

<210> SEQ ID NO 9
<211> LENGTH: 19
<212> TYPE: DNA
<213> ORGANISM: Artificial Sequence
<220> FEATURE:
<223> OTHER INFORMATION: Inner Probe K

<400> SEQUENCE: 9
agcttggagg cttgaacag                                                  19

<210> SEQ ID NO 10
<211> LENGTH: 23
<212> TYPE: DNA
<213> ORGANISM: Artificial Sequence
<220> FEATURE:
<223> OTHER INFORMATION: Reverse Primer K3

<400> SEQUENCE: 10
ggaaagaagt cagaaggcaa aaa                                             23

<210> SEQ ID NO 11
<211> LENGTH: 20
<212> TYPE: DNA
<213> ORGANISM: Artificial Sequence
<220> FEATURE:
<223> OTHER INFORMATION: Primer P

<400> SEQUENCE: 11
cctctgggat tctttcccga                                                 20

<210> SEQ ID NO 12
<211> LENGTH: 18
<212> TYPE: DNA
<213> ORGANISM: Artificial Sequence
<220> FEATURE:
<223> OTHER INFORMATION: Inner Probe Q

<400> SEQUENCE: 12
ctgagggctc caccccaa                                                   18

<210> SEQ ID NO 13
<211> LENGTH: 19
<212> TYPE: DNA
<213> ORGANISM: Artificial Sequence
<220> FEATURE:
<223> OTHER INFORMATION: Primer Rr

<400> SEQUENCE: 13
```

```
cactgcatgg cctgaggat                                                19
```

```
<210> SEQ ID NO 14
<211> LENGTH: 24
<212> TYPE: DNA
<213> ORGANISM: Artificial Sequence
<220> FEATURE:
<223> OTHER INFORMATION: Primer Rf

<400> SEQUENCE: 14
tcatcctcag gccatgcagt ggaa                                          24

<210> SEQ ID NO 15
<211> LENGTH: 18
<212> TYPE: DNA
<213> ORGANISM: Artificial Sequence
<220> FEATURE:
<223> OTHER INFORMATION: Inner Probe A

<400> SEQUENCE: 15
gaactggagc caccagca                                                 18

<210> SEQ ID NO 16
<211> LENGTH: 27
<212> TYPE: DNA
<213> ORGANISM: Artificial Sequence
<220> FEATURE:
<223> OTHER INFORMATION: Primer Br

<400> SEQUENCE: 16
cccctagaaa attgagagaa gtccacc                                       27

<210> SEQ ID NO 17
<211> LENGTH: 17
<212> TYPE: DNA
<213> ORGANISM: Artificial Sequence
<220> FEATURE:
<223> OTHER INFORMATION: Inner Probe C2

<400> SEQUENCE: 17
gccaaaattc gcagtcc                                                  17

<210> SEQ ID NO 18
<211> LENGTH: 19
<212> TYPE: DNA
<213> ORGANISM: Artificial Sequence
<220> FEATURE:
<223> OTHER INFORMATION: Inner Probe C3

<400> SEQUENCE: 18
ggccaaaatt cgcagtccc                                                19

<210> SEQ ID NO 19
<211> LENGTH: 16
<212> TYPE: DNA
<213> ORGANISM: Artificial Sequence
<220> FEATURE:
<223> OTHER INFORMATION: Inner Probe C5

<400> SEQUENCE: 19
ccaaaattcg cagtcc                                                   16

<210> SEQ ID NO 20
<211> LENGTH: 17
<212> TYPE: DNA
<213> ORGANISM: Artificial Sequence
```

```
<220> FEATURE:
<223> OTHER INFORMATION: Inner Probe C6

<400> SEQUENCE: 20
ccaaaattcg cagtccc                                                          17

<210> SEQ ID NO 21
<211> LENGTH: 26
<212> TYPE: DNA
<213> ORGANISM: Artificial Sequence
<220> FEATURE:
<223> OTHER INFORMATION: Molecular Beacon Probe C

<400> SEQUENCE: 21
ccgagtggcc aaaattcgca gctcgg                                                26

<210> SEQ ID NO 22
<211> LENGTH: 30
<212> TYPE: DNA
<213> ORGANISM: Artificial Sequence
<220> FEATURE:
<223> OTHER INFORMATION: Molecular Beacon Probe I

<400> SEQUENCE: 22
ctgcgagtcc aagagtcctc ttatgcgcag                                            30

<210> SEQ ID NO 23
<211> LENGTH: 29
<212> TYPE: DNA
<213> ORGANISM: Artificial Sequence
<220> FEATURE:
<223> OTHER INFORMATION: Molecular Beacon Probe K

<400> SEQUENCE: 23
cgcttagctt ggaggcttga acagaagcg                                             29

<210> SEQ ID NO 24
<211> LENGTH: 28
<212> TYPE: DNA
<213> ORGANISM: Artificial Sequence
<220> FEATURE:
<223> OTHER INFORMATION: Molecular Beacon Probe Q

<400> SEQUENCE: 24
cgcagctgag ggctccaccc caactgcg                                              28

<210> SEQ ID NO 25
<211> LENGTH: 28
<212> TYPE: DNA
<213> ORGANISM: Artificial Sequence
<220> FEATURE:
<223> OTHER INFORMATION: Molecular Beacon Probe A

<400> SEQUENCE: 25
cgctcgaact ggagccacca gcagagcg                                              28

<210> SEQ ID NO 26
<211> LENGTH: 25
<212> TYPE: DNA
<213> ORGANISM: Artificial Sequence
<220> FEATURE:
<223> OTHER INFORMATION: Molecular Beacon Probe C2

<400> SEQUENCE: 26
ccgagccaaa attcgcagtc ctcgg                                                 25
```

<210> SEQ ID NO 27
<211> LENGTH: 27
<212> TYPE: DNA
<213> ORGANISM: Artificial Sequence
<220> FEATURE:
<223> OTHER INFORMATION: Molecular Beacon Probe C3

<400> SEQUENCE: 27
ccgaggccaa aattcgcagt ccctcgg                                    27

<210> SEQ ID NO 28
<211> LENGTH: 25
<212> TYPE: DNA
<213> ORGANISM: Artificial Sequence
<220> FEATURE:
<223> OTHER INFORMATION: Molecular Beacon Probe C4

<400> SEQUENCE: 28
cgaggccaaa attcgcagtc cctcg                                      25

<210> SEQ ID NO 29
<211> LENGTH: 26
<212> TYPE: DNA
<213> ORGANISM: Artificial Sequence
<220> FEATURE:
<223> OTHER INFORMATION: Molecular Beacon Probe C5

<400> SEQUENCE: 29
ccgatccaaa attcgcagtc catcgg                                     26

<210> SEQ ID NO 30
<211> LENGTH: 29
<212> TYPE: DNA
<213> ORGANISM: Artificial Sequence
<220> FEATURE:
<223> OTHER INFORMATION: Molecular Beacon Probe C6

<400> SEQUENCE: 30
cgaccaacca aaattcgcag tcccggtcg                                  29

<210> SEQ ID NO 31
<211> LENGTH: 806
<212> TYPE: DNA
<213> ORGANISM: Artificial Sequence
<220> FEATURE:
<223> OTHER INFORMATION: Control Sequence

<400> SEQUENCE: 31
tttgctcaca tgttctttcc tgcgttatcc cctgawtctg tggataaccg tattaccgcc    60
tttgagtgag ctgataccgc tcgccgcagc cgaacgaccg agcgcagcga gtcagtgagc   120
gaggaagcgg aagagcgccc aatacgcaaa ccgcctctcc ccgcgcgttg gccgattcat   180
taatgcaggt taacctggct tatcgaaatt aatacgactc actatagggg gaccggcaga   240
tctgatatca tcgatgaatt cagagtctag actcgtggtg gacttcttgg agctggtcgt   300
attggatctg cttatgcaag aatgatggta gaagggttta agatgaacct gatctacttt   360
gatctttatc agtcaaccag gctcgaaaag ttcgttacag cctatggcga gttcctaaaa   420
gccaacggtg aggttccatc ctgctgctat gcctcatctt cttgtcgacc tgcaggcatg   480
caagcttcag ctgctcgagt tctatagtgt cacctaaatc gtatgtgtat gatacataag   540
gttatgtatt aattgtagcc gcgttctaac gacaatatgt ccatatggtg cactctcagt   600
acaatctgct ctgatgccgc atagttaagc cagccccgac accgccaac acccgctgac    660

```
gcgccctgac gggcttgtct gctcccggca tccgcttaca gacaagctgt gaccgtctcc    720
gggagctgca tgtgtcagag gttttcaccg tcatcaccga aacgcgcgag acgaaagggc    780
ctcgtgatac gcctattttt ataggt                                         806

<210> SEQ ID NO 32
<211> LENGTH: 202
<212> TYPE: DNA
<213> ORGANISM: Artificial Sequence
<220> FEATURE:
<223> OTHER INFORMATION: Control Sequence

<400> SEQUENCE: 32
agagtctaga ctcgtggtgg acttcttgga gctggtcgta ttggatctgc ttatgcaaga     60
atgatggtag aagggtttaa gatgaacctg atctactttg atctttatca gtcaaccagg    120
ctcgaaaagt tcgttacagc ctatggcgag ttcctaaaag ccaacggtga ggttccatcc    180
tgctgctatg cctcatcttc tt                                             202

<210> SEQ ID NO 33
<211> LENGTH: 36
<212> TYPE: DNA
<213> ORGANISM: Artificial Sequence
<220> FEATURE:
<223> OTHER INFORMATION: Control Probe Bic26

<400> SEQUENCE: 33
cgcgactttg atctttatca gtcaaccagg ctcgcg                               36

<210> SEQ ID NO 34
<211> LENGTH: 32
<212> TYPE: DNA
<213> ORGANISM: Artificial Sequence
<220> FEATURE:
<223> OTHER INFORMATION: Control Probe Bic26b

<400> SEQUENCE: 34
cgacctttga tctttatcag tcaaccaggt cg                                   32
```